US012808234B1

(12) United States Patent
Wriggle

(10) Patent No.: US 12,808,234 B1
(45) Date of Patent: Nov. 24, 2026

(54) DETAINEE MONITOR RESTRAINT

(71) Applicant: Steven D. Wriggle, Schertz, TX (US)

(72) Inventor: Steven D. Wriggle, Schertz, TX (US)

( * ) Notice: Subject to any disclaimer, the term of this patent is extended or adjusted under 35 U.S.C. 154(b) by 28 days.

(21) Appl. No.: 19/068,387

(22) Filed: Mar. 3, 2025

Related U.S. Application Data

(62) Division of application No. 18/199,407, filed on May 19, 2023, now abandoned.

(51) Int. Cl.
*E05B 75/00* (2006.01)
*A61F 5/37* (2006.01)

(52) U.S. Cl.
CPC ................ *E05B 75/00* (2013.01); *A61F 5/37* (2013.01)

(58) Field of Classification Search
CPC .................................. E05B 75/00; A61F 5/37
See application file for complete search history.

(56) References Cited

U.S. PATENT DOCUMENTS

| | | | | |
|---|---|---|---|---|
| 4,287,731 A * | 9/1981 | Kruger | E05B 75/00 70/16 |
| 4,617,810 A | 10/1986 | Fish et al. | |
| 4,748,875 A | 6/1988 | Lang | |
| 7,316,137 B2 * | 1/2008 | Parsons | E05B 75/00 70/432 |
| 8,353,183 B1 * | 1/2013 | Lofgren | E05B 75/00 70/16 |
| 8,839,796 B2 | 9/2014 | Resse et al. | |
| 2017/0010663 A1 | 1/2017 | Tanaka et al. | |
| 2023/0141400 A1 * | 5/2023 | Rebro | A61B 5/0022 600/301 |

FOREIGN PATENT DOCUMENTS

| | | | |
|---|---|---|---|
| CN | 202544575 U * | 11/2012 | |
| CN | 203570036 U * | 4/2014 | |
| CN | 205451381 U * | 8/2016 | |
| CN | 206309163 U * | 7/2017 | |
| CN | 111411838 A * | 7/2020 | E05B 75/00 |
| CN | 211818780 U * | 10/2020 | |
| WO | WO-2024065027 A1 * | 4/2024 | E05B 75/00 |

OTHER PUBLICATIONS

Espacenet machine generated translation of CN 111411838 A. (Year: 2026).*

* cited by examiner

*Primary Examiner* — Kristina R Fulton
*Assistant Examiner* — Emily G. Brown
(74) *Attorney, Agent, or Firm* — Donald J. Ersler

(57) ABSTRACT

A detainee monitor restraint preferably includes a detainee restraint and a law enforcement control device. The detainee restraint preferably includes a first cuff member, a second cuff member, a cuff connecting member and a monitoring device. The cuff connecting member connects the first cuff member to the second cuff member. The monitoring device is retained on one of the base members. The monitoring device preferably includes a microprocessor-based circuit, a plurality of body sensors, a transceiver and a battery. The monitoring device preferably uses Photoplethysmography technology, such that the monitoring device does not need to be contact with a wrist. A linear ratchet with a key release or a rotary cam lock with key release may be used to force the monitoring device against a wrist. A rotary cam rachet is turned to force the monitoring device against a wrist. A handcuff key is used to release the monitoring device.

10 Claims, 5 Drawing Sheets

DETAINEE MONITOR RESTRAINT

CROSS-REFERENCES TO RELATED APPLICATIONS

This is a divisional patent application, which takes priority from patent application Ser. No. 18/199,407, filed on May 19, 2023.

BACKGROUND OF THE INVENTION

Field of the Invention

The present invention relates generally to law enforcement detention and more specifically to a detainee monitor restraint, which improves upon prior art handcuffs, while providing the addition of monitoring features.

Discussion of the Prior Art

Billions of dollars are spent annually in lawsuits, because restrained individuals suffer medical issues and are injured or die because of the restraint. The technology of monitoring individuals for health issues is currently available. Many times, those who have committed a crime may be experiencing mental health, neurologic, elicit or prescribed drug induced issues. With physiological, neurologic, physical, or underlying health problems whether revealed, known, or not known. Law enforcement officers are not emergency medical technicians (EMT), they are provided basics (bleeding control, stabilization, CPR/AED. While part of law enforcements routine training includes this basic training, dealing with or recognizing real health issues such as underlying complications in the field or during transport i.e., (neurologic, vascular, cardiac, pulmonary etc.) is dedicated those trained such EMT Paramedics.

During apprehension and while subduing a suspect; both officer of the law and the detainee are experiencing "extreme" biological and physiological effects, such as an adrenaline rush. In addition, to the medical and knowledge issues mentioned above, the present invention is predicated again on retraining high risk detainees, and mitigating known methodologies for escaping. The methods of escape include breakage or slipping out of the restraints, the commonly used linked chain or the chains interior retainer pin, picking the locking mechanism, and faking health or medical conditions while wearing the restraints. Law enforcement has adopted the use of body-worn cameras. However, body-worn cameras do not help in post capture and detainment. U.S. Pat. No. 4,287,731 to Kruger discloses handcuffs. U.S. Pat. No. 4,748,875 to Lang discloses a ratchet box wrench with offset handle. Patent publication no. 2017/0010663 to Tanaka et al. discloses smart wearable devices and methods for optimizing output. U.S. Pat. No. 8,839,796 to Resse et al. discloses an apparatus and system for augmented detainee restraint.

Accordingly, there is clearly felt need in the art for a detainee monitor restraint, provides feedback of the health of the detainee; the location of the detainee; and reduce or mitigate liability from detainee lawsuits.

SUMMARY OF THE INVENTION

The present invention provides a detainee monitor restraint, which improves upon prior art handcuffs, while providing the addition of monitoring features. The detainee monitor restraint preferably includes a detainee restraint and a law enforcement control device. The detainee restraint preferably includes a first cuff member, a second cuff member, a cuff connecting member, a monitoring device and a shocking device also known as a Taser®. Each cuff member preferably includes a base member and a ratcheting arm. The base member includes a base portion and an arm portion. The arm portion includes a substantially semi-circular shape. The arm portion extends outward from the base portion. The ratcheting arm includes a substantially semi-circular shape. One end of the ratcheting arm is preferably pivotally connected to an opposing end of the arm portion. An opposing end of the ratcheting arm portion includes a plurality of ratchet teeth. A recessed key lock for unlocking the ratcheting arm is preferably formed in the base member. U.S. Pat. No. 4,748,875 discloses a rotary ratchet, which is herein incorporated by reference in its entirety. The pawl 60 may be released by use of a handcuff key inserted into an adjacent recessed key lock. A base ratchet pawl is located in the base member. The ratchet pawl is released with a handcuff key inserted into a base key lock cavity. U.S. Pat. No. 4,287,731 illustrates a rachet pawl locking mechanism, which is hereby incorporated by reference in its entirety. However, other types of locking mechanisms may also be used. U.S. Pat. No. 11,434,668 to Wriggle et al. is hereby incorporated by reference in its entirety.

The cuff connecting member is any suitable device that connects the first and second cuffs together, such as that disclosed in U.S. Pat. No. 11,434,668, which is hereby incorporated by reference in its entirety. However, other types of cuff connecting members may also be used. The monitoring device is attached to the base member of one of the cuff members with any suitable method, such as adhesive or fasteners. The monitoring device utilizes Photoplethysmography (PPG) technology to detect volumetric changes in blood in peripheral circulation. The PPG technology does not require that sensors contact skin to provide a reading of a person's body vitals.

In a second embodiment, the monitoring device is slidably engaged with the base member with rails or the like. The second embodiment of the monitoring device does not utilize PPG technology. A linear ratchet with a key release is used to lock the monitoring device against a wrist of the person wearing the handcuffs. The linear ratchet with key release is similar to a sliding glass door lock disclosed in U.S. Pat. No. 4,617,810, which is hereby incorporated by reference in its entirety. The linear ratchet with key release preferably includes a ratchet housing ratchet and a rachet arm. The rachet housing includes a spring-loaded pawl, a bottom slot for receiving the ratchet arm and a key slot for receiving a handcuff key. The ratchet arm includes a plurality of serrated edges. The rachet housing is attached to the base member with any suitable method. One end of the rachet arm is slidably retained in the ratchet housing and the other end is secured to the monitoring device. When the first cuff is secured to a detainee's wrist, the monitoring device is pushed against the detainee's wrist. The spring-loaded pawl does not allow the ratchet arm to be pushed away from the detainee's wrist.

In order to retract the monitoring device relative to the detainee's wrist, a handcuff key is inserted in the key slot. The handcuff key is turned to pull the spring-loaded pawl away from the plurality of serrated edges. The user turns the handcuff key to pull the spring-load pawl back and simultaneously slides the monitoring device away from detainee's wrist.

In a third embodiment, the monitoring device is slidably engaged with the base member with rails or the like. The third embodiment of the monitoring device does not utilize PPG technology. A rotary cam lock with key release is used to lock the monitoring device against a detainee's wrist. The rotary cam lock with key release preferably includes a rotary cam ratchet, a spring-loaded pawl and a ratchet cover. The rotary cam ratchet includes a cam member, a twist knob and a cam projection. The cam projection extends from one side of the cam member and a plurality of serrated indentations are formed in an opposing side of the cam member. The twist knob extends from a top of the cam member. The cam projection is rotatably engaged with a curved depression in the base member.

The spring-loaded pawl includes a pivot base, a pawl projection and a torsion spring. The pivot base includes a key cavity, which is sized to receive an end of the handcuff key. The pawl projection extends from a side of the pivot base and is shaped to engage the plurality of serrated indentations formed in the cam member. The pawl projection is biased against the cam member with the torsion spring. The torsion spring is also engaged with the base member. The ratchet cover includes a top wall, a first side wall and a second side wall. The top wall covers the rotary cam lock with key release and partially covers the monitoring device. A knob hole is formed through the top wall to receive the twist knob and a key opening is formed through the top wall to receive the handcuff key.

The shocking device is preferably retained in the monitoring device. The monitoring device preferably includes a microprocessor-based circuit, a plurality of sensors, a transceiver and a battery. A software program is installed in the microprocessor-based circuit to receive data from the plurality of sensors. The sensor data received is compared to existing ranges of normal physiological parameters. If the detainee's physiological data is outside the normal physiological parameters, an alert is sent to a law enforcement monitoring device through the transceiver. It is preferable that the plurality of sensors monitor pulse oximeter, blood oxygen saturation, skin and body temperature, heart rate, blood glucose, blood sugar level, respiration rate blood cortisol, blood pressure, electrocardiogram (ECG), pedometer, body positioning and movement. It is preferable that the monitoring device alert law enforcement through the plurality of sensors to prevent undesirable health conditions. Further, physiological sensor data may be used to form a profile of whether a detainee intends to attempt a violent confrontation; escape; or about to experience a serious medical condition. Additionally, the sensor data can be used in court to attribute the cause of the injuries sustained, while wearing the detainee monitor restraint to detainee self-inflicted injuries, mishandling by law enforcement or some other factor. The above data could be used to send an alert to law enforcement. The shocking device is used to control an unruly detainee. The shocking device is preferably a miniaturized version of a prior art shocking device.

It is preferable that the monitoring device use (GPS) to monitor the location of a detainee, if they should escape or become lost. The software program should also be capable of checking each sensor for functionality. It is preferable that the monitoring device be controlled by the law enforcement control device. The law enforcement control device is preferably some type of electronic device, such as a laptop computer or smart phone to eliminate any controls being accessible by the detainee. A key fob or the law enforcement control device may be used to activate the shocking device.

The transceiver may communicate through any suitable wireless protocol, such as WiFi, Bluetooth, cellular or the like.

Accordingly, it is an object of the present invention to provide a detainee monitor restraint, which provides feedback of the health of the detainee; and the location of the detainee.

Finally, it is another object of the present invention to provide a detainee monitor restraint, which reduces or mitigate liability from detainee lawsuits.

These and additional objects, advantages, features and benefits of the present invention will become apparent from the following specification.

DETAILED DESCRIPTION OF THE PREFERRED EMBODIMENTS

Figure 1:
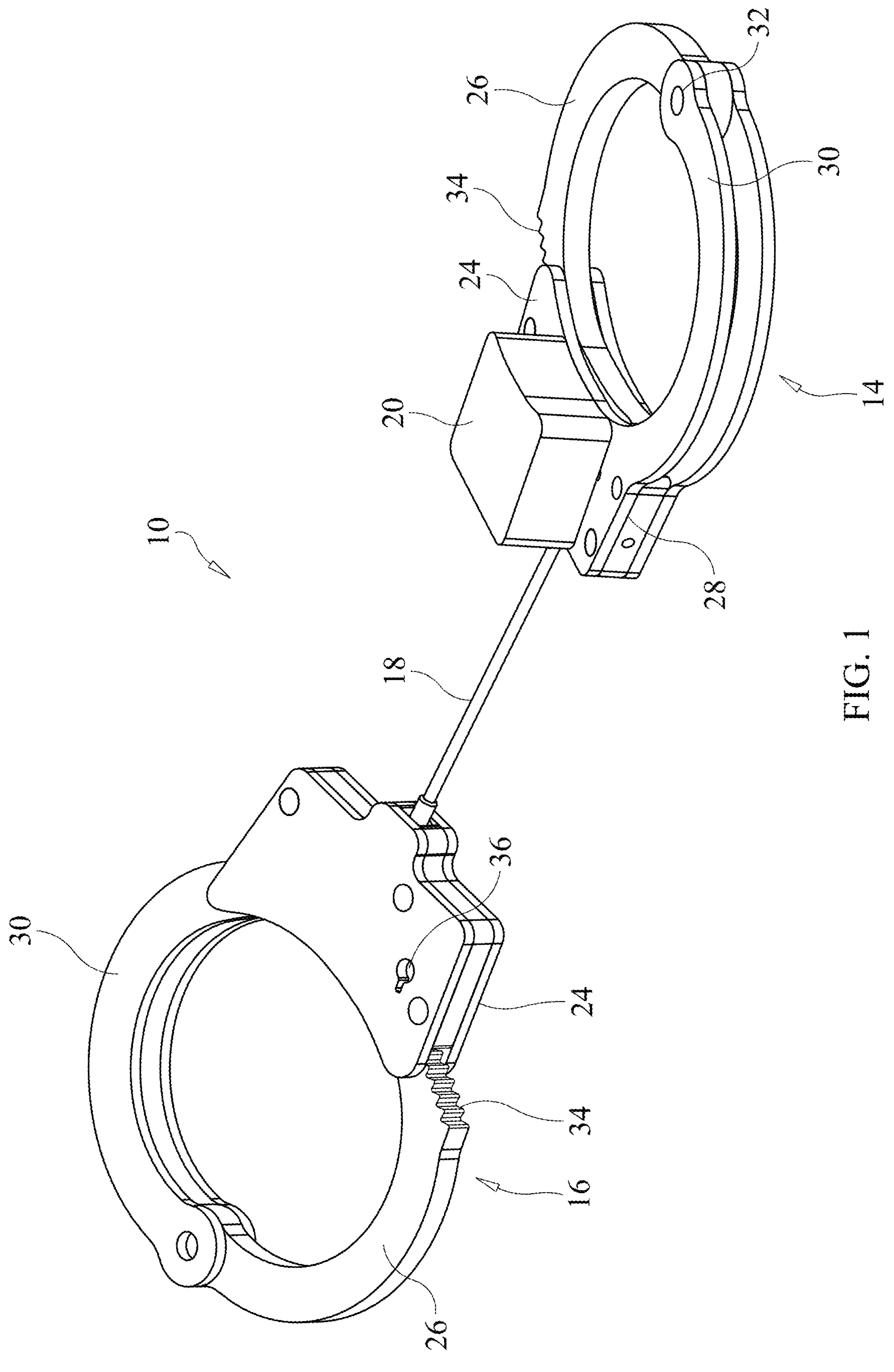
FIG. 1 is a top perspective view of a detainee restraint monitor with a monitor restrain utilizing Photoplethysmography technology in accordance with the present invention.
Figure 5:
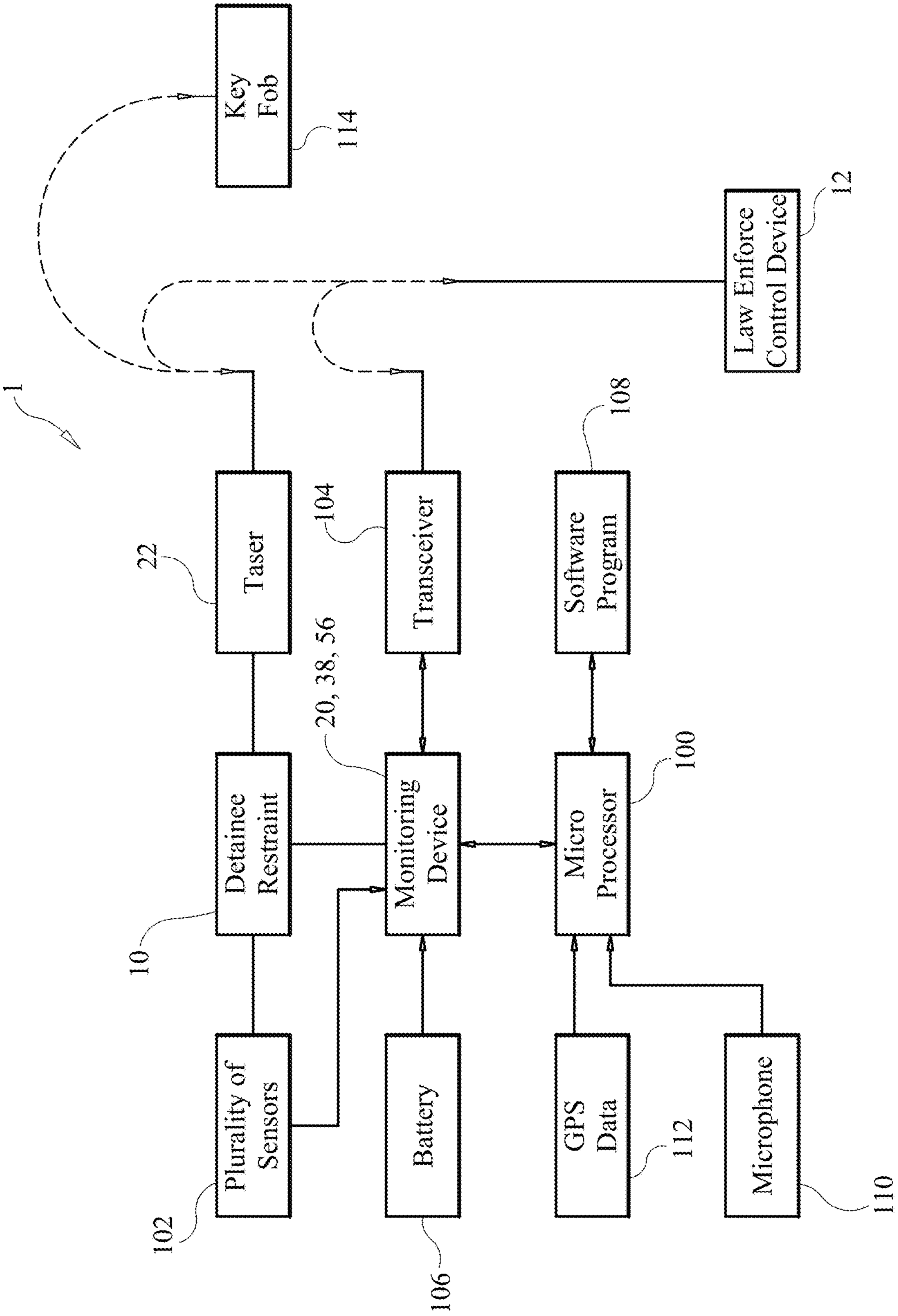
FIG. 5 is a schematic diagram of a detainee restraint monitor in accordance with the present invention.

With reference now to the drawings, and particularly to FIG. 5, there is shown a schematic diagram of a detainee restraint device 1. The detainee monitor restraint 1 preferably includes a detainee restraint 10 and a law enforcement control device 12. With reference to FIG. 1, the detainee restraint 10 preferably includes a first cuff member 14, a second cuff member 16, a cuff connecting member 18, a monitoring device 20 and a shocking device 22. Each cuff member 14, 16 preferably includes a base member 24, and a ratcheting arm 26. The base member 24 includes a base portion 28 and an arm portion 30. The arm portion 30 includes a curved length. The arm portion 30 extends outward from the base portion 28. The ratcheting arm 26 includes a curved length. One end of the ratcheting arm 26 is pivotally connected to an end of the arm portion 28 at a pivot point 32. A plurality of ratchet teeth 34 are formed on an opposing end of the ratcheting arm 26. A recessed key lock 36 for unlocking the ratcheting arm is formed in the base member 24.

U.S. Pat. No. 4,748,875 discloses a rotary ratchet, which herein is incorporated by reference in its entirety. With application to a hand cuff, the pawl 60 may be released by use of a handcuff key inserted into an adjacent recessed key lock. Concerning applicant's invention, a base ratchet pawl (not shown) is located in the base member 24. The ratchet pawl is released with a handcuff key 52 inserted into a base key lock cavity 36. U.S. Pat. No. 4,287,731 illustrates a rachet pawl locking mechanism, which is hereby incorporated by reference in its entirety. The cuff connecting member 18 is any suitable device that connects the first and second cuffs 14, 16 together, such as that disclosed in U.S. Pat. No. 11,434,668, which is hereby incorporated by reference in its entirety. However, other types of cuff connecting members may also be used.

With reference to FIG. 1, the monitoring device 20 is attached to the base member 24 of one of the cuff members 14, 16 with any suitable method, such as adhesive or fasteners. The monitoring device 20 utilizes Photoplethysmography (PPG) technology to detect volumetric changes in blood in peripheral circulation of the detainee. The PPG technology does not require that sensors contact the skin of a detainee to provide a reading of the detainee's body vitals.

Figure 2:
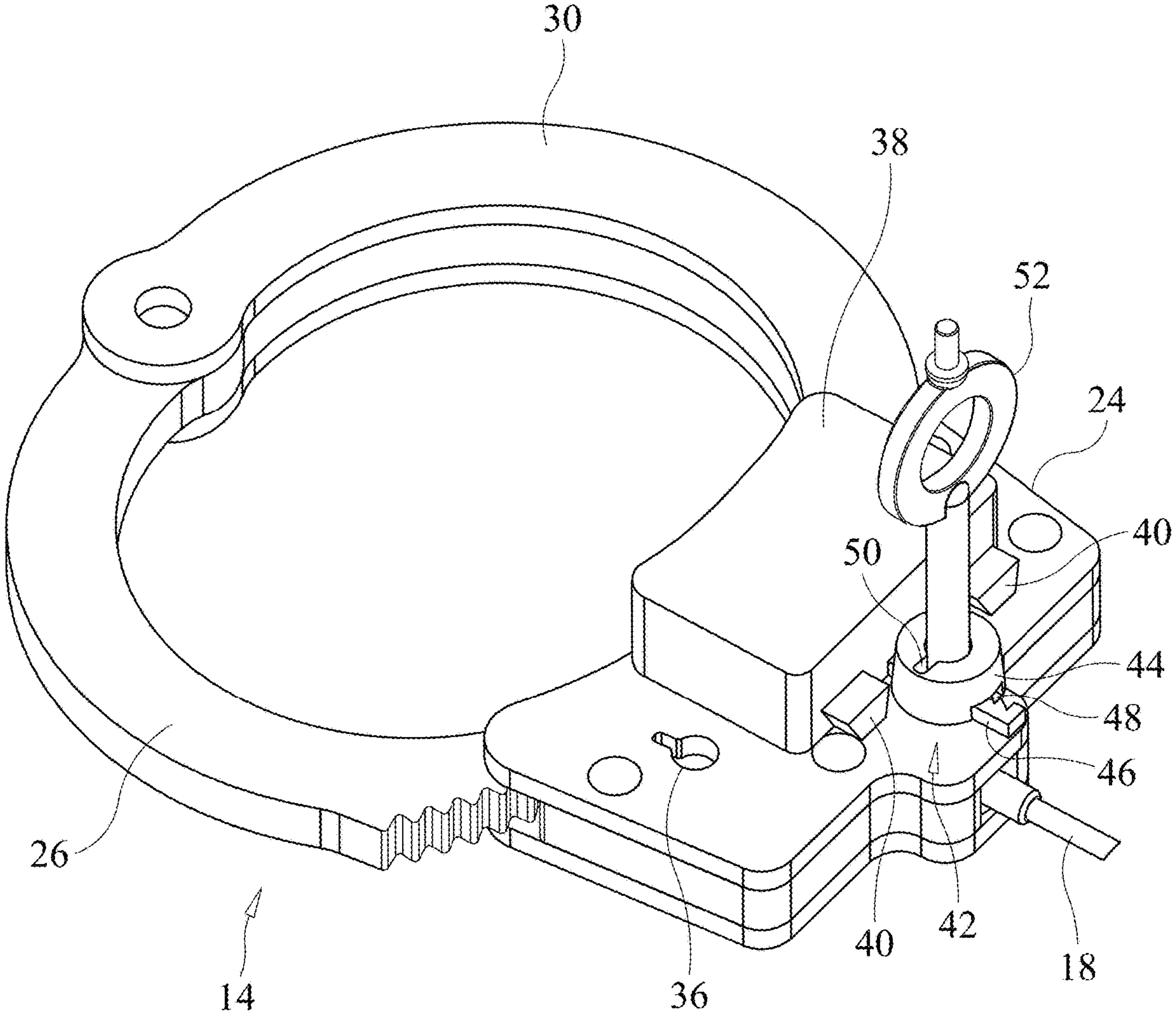
FIG. 2 is a top perspective view of a single cuff of a detainee restraint monitor with a monitor restrain having a linear ratchet with a key release used to lock the monitoring device against a detainee's wrist in accordance with the present invention.

With reference to FIG. 2, a second embodiment of the monitoring device 38 is slidably engaged with the base member 24 with dovetail rails 40 or any other suitable slide retention system. The dovetail rails 40 may be secured to the base member 24 with fasteners or the like. The monitoring device 38 does not utilize PPG technology. A linear ratchet 42 with a key release 44 is used to lock the monitoring device 38 against a wrist of the detainee. The linear ratchet with key release 42 is similar to a sliding glass door lock disclosed in U.S. Pat. No. 4,617,810. The linear ratchet with key release 42 preferably includes a ratchet housing 44 and a rachet arm 46. The rachet housing 44 includes a spring-loaded pawl (not shown), a bottom slot 48 for receiving the ratchet arm 46 and a key slot 50 for receiving a handcuff key 52. The ratchet arm 46 includes a plurality of serrated edges 54. The rachet housing 44 is attached to the base member 24 with any suitable method. One end of the rachet arm 46 is slidably retained in the ratchet housing 44 and the other end is secured to the monitoring device 38. When the first cuff 14 is secured to a detainee's wrist, the monitoring device 38 is pushed against the detainee's wrist. The spring-loaded pawl does not allow the ratchet arm 46 to be pushed away from the detainee's wrist. In order to retract the monitoring device 38 relative to the detainee's wrist, the handcuff key 52 is inserted in the key slot 50. The handcuff key 52 is turned to pull the spring-loaded pawl away from the plurality of serrated edges 54. The user turns the handcuff key 52 to pull the spring-load pawl back and simultaneously slides the monitoring device 38 away from the detainee's wrist.

Figure 3:
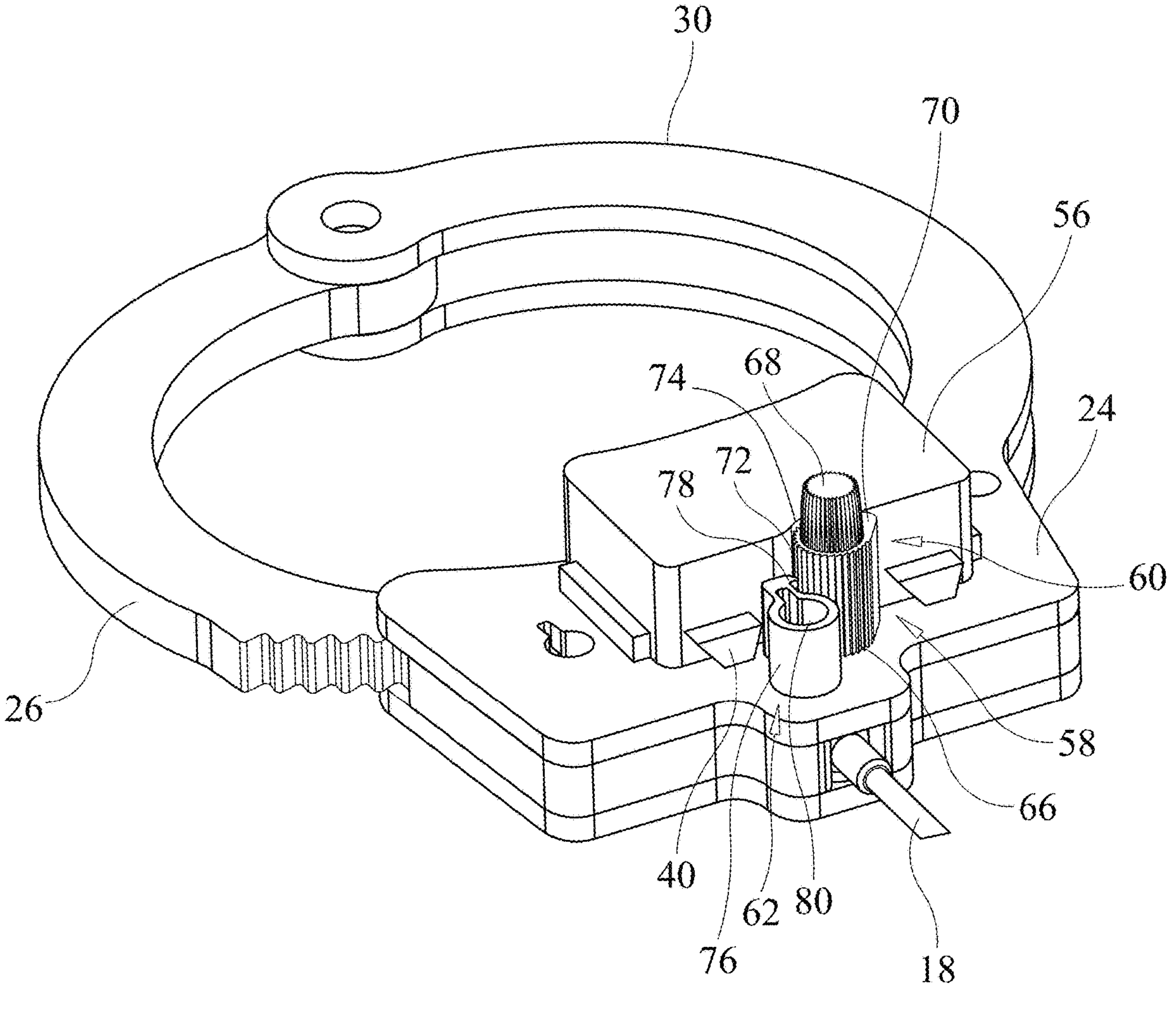
FIG. 3 is a top perspective view of a single cuff of a detainee restraint monitor with a rotary cam lock with key release used to lock the monitoring device against a detainee's wrist with a ratchet cover removed in accordance with the present invention.
Figure 4:
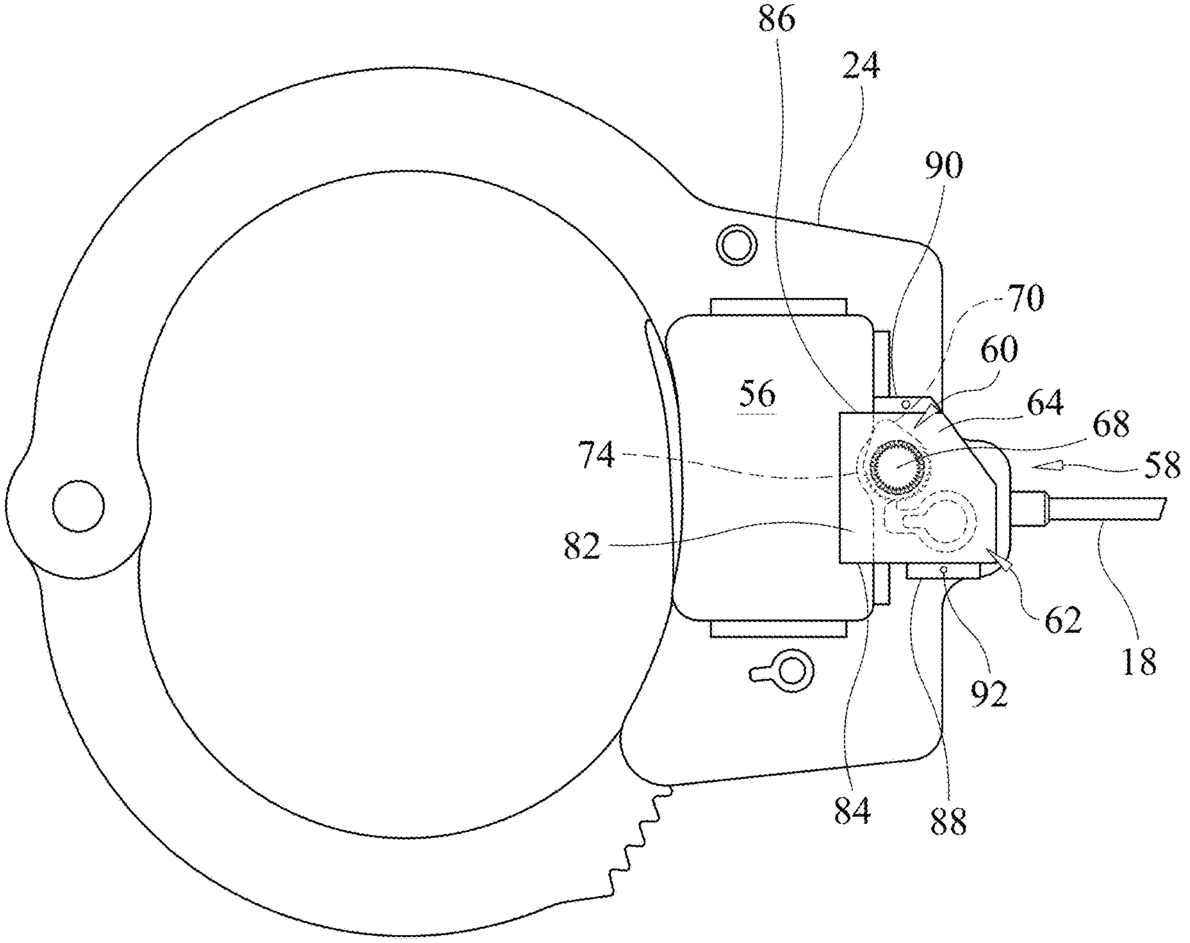
FIG. 4 is a top view of a single cuff of a detainee restraint monitor with a cover placed over a rotary cam lock with key release used to lock the monitoring device against a detainee's wrist in accordance with the present invention.

With reference to FIGS. 3-4, a third embodiment of the monitoring device 56 is slidably engaged with the base member 24 with the dovetail rails 40 any other suitable slide retention system. The monitoring device 56 does not utilize PPG technology. A rotary cam lock with key release 58 is used to lock the monitoring device 56 against a detainee's wrist. The rotary cam lock with key release 58 preferably includes a rotary cam ratchet 60, a spring-loaded pawl 62 and a ratchet cover 64. The rotary cam ratchet 60 includes a cam member 66, a twist knob 68 and a cam projection 70. The cam projection 70 extends from one side of the cam member 66 and a plurality of serrated indentations 72 are formed in an opposing side of the cam member 66. The twist knob 68 extends from a top of the cam member 66. The cam projection 70 is rotatably engaged with a curved depression 74 formed in an end of the monitoring device 56.

The spring-loaded pawl 62 includes a pivot base 76, a pawl projection 78 and a torsion spring (not shown). The pivot base 76 is pivotally secured to the base member 24. A key cavity 80 is formed in a top of the pivot base 76 to receive an end of the handcuff key 52. The pawl projection 78 extends from a side of the pivot base 76 and is shaped to engage the plurality of serrated indentations 72 formed in the cam member 66. The pawl projection 78 is biased against the cam member 66 with the torsion spring. The torsion spring is also engaged with the base member 24. The ratchet cover 64 preferably includes a top wall 82, a first side wall 84 and a second side wall 86. The top wall 82 covers the rotary cam lock with key release 58 and a portion of the monitoring device 56. A knob hole is formed through the top wall 82 to receive the twist knob 68 and a key opening is formed through the top wall 82 to receive the handcuff key 52. A first mounting member 88 extends outward from a bottom of the first side wall 84. A second mounting member 90 extends outward from a bottom of the second side wall 86. The first and second mounting members 88, 90 are preferably secured to the base member 24 with at least one fastener 92.

With reference to FIG. 5, the shocking device 22 is preferably retained in the monitoring device 20, 38, 56, but could be a stand-alone device mounted to an opposing cuff member 14, 16.

The monitoring device 20, 38, 56 preferably includes a microprocessor-based circuit 100, a plurality of body sensors 102, a transceiver 104 and a battery 106. A software program 108 is installed in the microprocessor-based circuit 100 to receive data from the plurality of sensors 102. Sensor data received from the plurality of sensors 102 is compared to existing ranges of normal physiological parameters. If the detainee's physiological data is outside the normal physiological parameters, an alert is sent to the law enforcement monitoring device 12 through the transceiver 104. It is preferable that the plurality of sensors 102 monitor pulse oximeter, blood oxygen saturation, skin and body temperature, heart rate, blood glucose, blood sugar level, respiration rate blood cortisol, blood pressure, electrocardiogram (ECG), pedometer, body positioning and movement. It is preferable that the monitoring device 12 alert law enforcement through the plurality of sensors 102 to prevent undesirable health conditions from affecting the detainee. Further, physiological sensor data may be used to form a profile of whether a detainee intends to attempt a violent confrontation or escape. Additionally, the sensor data can be used in court to attribute the cause of the injuries sustained, while wearing detainee monitor restraint to detainee self-inflicted injuries, mishandling by law enforcement or some other factor. The above data could also be used to send an alert to law enforcement. The shocking device 22 is used to control an unruly detainee. The shocking device 22 is preferably a miniaturized version of a prior art shocking device. A microphone 110 is preferably connected to the microprocessor 100 to provide a recording of the detainee or anyone near the detainee.

It is preferable that the monitoring device use GPS data 112 to track a location of a detainee, if they should become lost or if they should escape. The software program 108 should also be capable of checking each one of the plurality of sensors 102 for functionality. It is preferable that the monitoring device 20, 38, 56 be controlled by the law enforcement control device 12. The law enforcement control device 12 is some type of electronic device, such as a laptop computer or smart phone to eliminate any controls being accessible by the detainee. A key fob 114 or the law enforcement control device 12 may be used to activate the shocking device 22. The transceiver 104 may communicate through any suitable wireless protocol, such as WiFi, Bluetooth, cellular or the like.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

What is claimed:

1. A detainee monitor restraint, comprising:

a first cuff member includes a first base member and a first ratcheting arm;

a second cuff member includes a second base member and a second ratcheting arm;

a cuff connecting member having one end secured to said first cuff member and a second end secured to said second cuff member; and a monitoring device is slidably retained relative to one of said first or second base members; and a rotary cam rachet is turned to force said monitoring device against a detainee wrist, a spring-loaded pawl engages said rotary cam ratchet to prevent release thereof; and said rotary cam ratchet includes a cam member and a cam projection, said cam projection extends from one side of said cam member and a plurality of serrated indentations are formed in an opposing side of said cam member, said spring loaded pawl includes a key slot for receiving a handcuff key, said spring loaded pawl engages said plurality of serrated indentations, wherein said spring loaded pawl is released by turning a handcuff key inserted therein.

2. The detainee monitor restraint of claim 1, further comprising:

at least one sensor for determining whether at least one physiological parameter of the body of a detainee is outside a normal physiological parameter.

3. The detainee monitor restraint of claim 2 wherein:

data from said at least one sensor is compared to existing ranges of normal physiological parameters, if the detainee's physiological data is outside normal physiological parameters, an alert is sent to a law enforcement monitoring device through said transceiver.

4. The detainee monitor restraint of claim 1, further comprising:

a control device is used to remotely control said detainee monitor restraint.

5. The detainee monitor restraint of claim 1 wherein:

said monitoring device is slidably retained with at least two rails mounted to at least one of said first or second base members.

6. A detainee monitor restraint, comprising:

a first cuff member includes a first base member and a first ratcheting arm;

a second cuff member includes a second base member and a second ratcheting arm;

a cuff connecting member having one end secured to said first cuff member and a second end secured to said second cuff member; and a monitoring device is slidably retained relative to one of said first or second base members;

a rotary cam rachet is turned to force said monitoring device against a detainee wrist, a spring-loaded pawl engages said rotary cam ratchet to prevent release thereof; and said rotary cam ratchet includes a cam member and a cam projection, said cam projection extends from one side of said cam member and a plurality of serrated indentations are formed in an opposing side of said cam member, said spring loaded pawl includes a key slot for receiving a handcuff key, said spring loaded pawl engages said plurality of serrated indentations, wherein said spring loaded pawl is released by turning a handcuff key inserted therein; and a rachet cover surrounds said spring loaded pawl.

7. The detainee monitor restraint of claim 6, further comprising:

at least one sensor for determining whether at least one physiological parameter of the body of a detainee is outside a normal physiological parameter.

8. The detainee monitor restraint of claim 7 wherein:

data from said at least one sensor is compared to existing ranges of normal physiological parameters, if the detainee's physiological data is outside normal physiological parameters, an alert is sent to a law enforcement monitoring device through said transceiver.

9. The detainee monitor restraint of claim 2, further comprising:

a control device is used to remotely control said detainee monitor restraint.

10. The detainee monitor restraint of claim 6 wherein:

said monitoring device is slidably retained with at least two rails mounted to at least one of said first or second base members.

* * * * *